United States Patent [19]
DelRe

[11] Patent Number: 5,101,835
[45] Date of Patent: Apr. 7, 1992

[54] METHOD AND APPARATUS FOR TESTING A SPINE

[76] Inventor: Lawrence DelRe, 174 Hollow Haven Dr., Pittsburgh, Pa. 15236

[21] Appl. No.: 572,433

[22] Filed: Aug. 27, 1990

[51] Int. Cl.⁵ ............................................. A61B 5/11
[52] U.S. Cl. ..................................... 128/781; 128/57; 33/512; 33/555
[58] Field of Search ............. 128/774, 781, 24.2, 128/24.3, 57, 60; 33/511, 512, 553, 554, 555, 449

[56] References Cited

U.S. PATENT DOCUMENTS

| | | | |
|---|---|---|---|
| 4,586,493 | 5/1986 | Goodman | 128/57 |
| 4,649,934 | 3/1987 | Fraser et al. | 128/774 |
| 4,762,134 | 8/1988 | Gala | 128/781 |
| 4,875,470 | 10/1989 | Cotone | 128/57 |
| 4,899,761 | 2/1990 | Brown et al. | 128/781 |
| 4,993,164 | 2/1991 | Jacobsen | 33/512 |

FOREIGN PATENT DOCUMENTS 2492250 4/1982 France .................. 128/781

Primary Examiner—Lee S. Cohen
Assistant Examiner—Krista M. Pfaffle
Attorney, Agent, or Firm—Martin J. Carroll

[57] ABSTRACT

A method for testing for dysfunctional discs in which a spinal contact member contacts a disc under a low force to obtain the position of the contact member with the disc in its normal or usual unstressed position, the same disc is contacted with the contact member under an elevated increased standard force to obtain a second position of the contact member, and the two positions are compared to determine the condition of the disc. A complete contour of the spine is obtained and recorded. Apparatus used includes a roller which bears against the spine and rolls from disc to disc with the roller being mounted on a vertical calibrated rod. Means are provided to vary the pressure applied to the rod.

15 Claims, 2 Drawing Sheets

METHOD AND APPARATUS FOR TESTING A SPINE

This invention relates to a method and apparatus for testing a spine and more particularly for testing for hypomobility and/or hypermobility of individual discs which is accomplished by motion-palpation and also for rotational intervertebral joint dysfunction.

Any two vertebrae adjacent to one another make up a "motor unit."

The function of a motor unit joining any two vertebrae to one another is dependent primarily upon the integrity of the disc that lies between the two vertebral bodies. The vertebral disc acts as a cushion, a shock absorber, and a joint. This is the anterior portion of a vertebral motor unit. The posterior portion of a vertebral motor unit is made up primarily of the facets. An upper and lower pair of both left and right facets meet with their mates from the vertebra above or below.

In the spine each vertebra has four facets with which it forms four separate facets joints. They may become fixated, stuck, or otherwise hypomobile. The facet joints generally do not become fixated unless the disc itself has become fixated, although it is conceivable that a moderate-to severe facet joint injury could immobilize a motor unit enough to cause fixation in the disc.

Even more posterior than the facet joints are the spinous processes; one extending to the posterior from each vertebra. These are the "bumps" that one sees running down the middle of one's back.

By pressing on a spinous process, one can indirectly test the resiliency of a particular disc, and its corresponding motor unit.

One way of testing is to have the patient lay down on his stomach and the doctor then using the heel of his hand, starting at the neck, repeatedly pushes slowly into the spinal column, works his way vertebra by vertebra to the bottom of the spine. The doctor looks for vertebra that are stuck (hypomobile) or loose (hypermobile). This method is too subjective and provides no hard-copy objective recording of the test.

One way of recording spinal motion objectively is to have the patient bend forward, backward and to each side while taking x-rays in each position. Severe intersegmental instability can be determined from the x-rays. This method has three disadvantages: (1) The resilience of each vertebral disc is not tested with pressure and so gives less information: (2) It only determines discs which are grossly unstable or fused; (3) It requires a great amount of radiation.

A third method utilizes a new computerized three-dimensional goniometer such as the METRECOM, manufactured by FARO of Canada. This includes a thin wand connected by an armature to a computer. The doctor touches the wand tip to the spinous process of each vertebra of a standing patient in an erect position and then again while bending forward. A reading is taken and recorded for each point touched and the computer allegedly figures out which vertebra are hyper or hypomobile. This system is very prone to the operator's error for several reasons so that it is not accurate. Thus it is only good for gross range-of-motion like any other goniometer. It also has the disadvantage of not testing under pressure.

It is therefore an object of my invention to provide an improved method for testing a human spine for hypomobility and/or hypermobility which also provides accurate, repeatable, and objective readings of a patient's spinal contour.

Another object is to provide such a method that shows the degree of flexibility, vertebra by vertebra, when a standard pressure is applied to each vertebra.

A further object is to provide such a method which gives information which enables the doctor to better diagnose a patient's problem and how to solve it.

A still further object is to provide a method of detecting rotational intervertebral dysfunction.

Still another object is to provide inexpensive apparatus suitable for use in carrying out my methods.

These objects and other objects will be more apparent after referring to the following specification and attached drawings in which.

Figure 1:
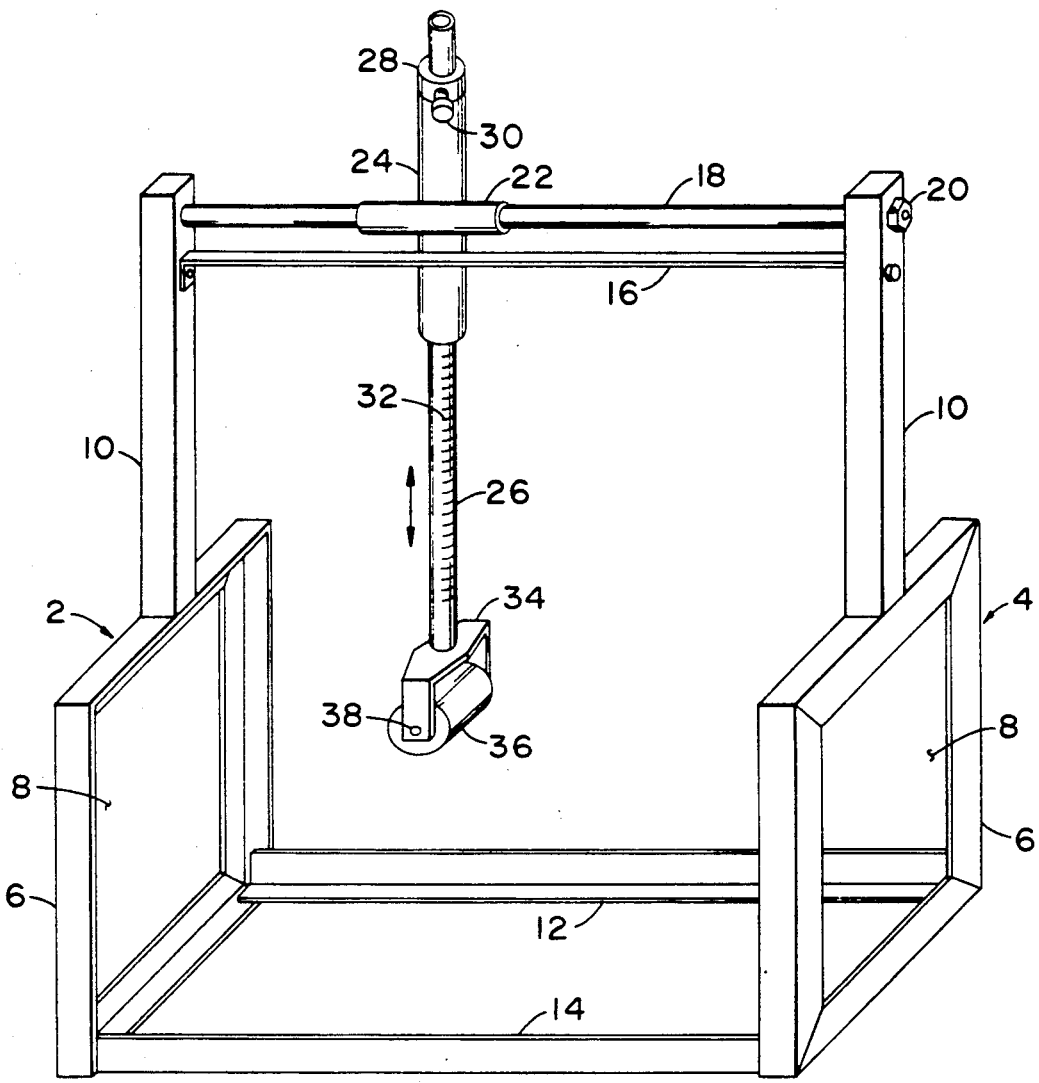
FIG. 1 is a perspective view of one embodiment of a spinal motion and resilience tester.
Figure 2:
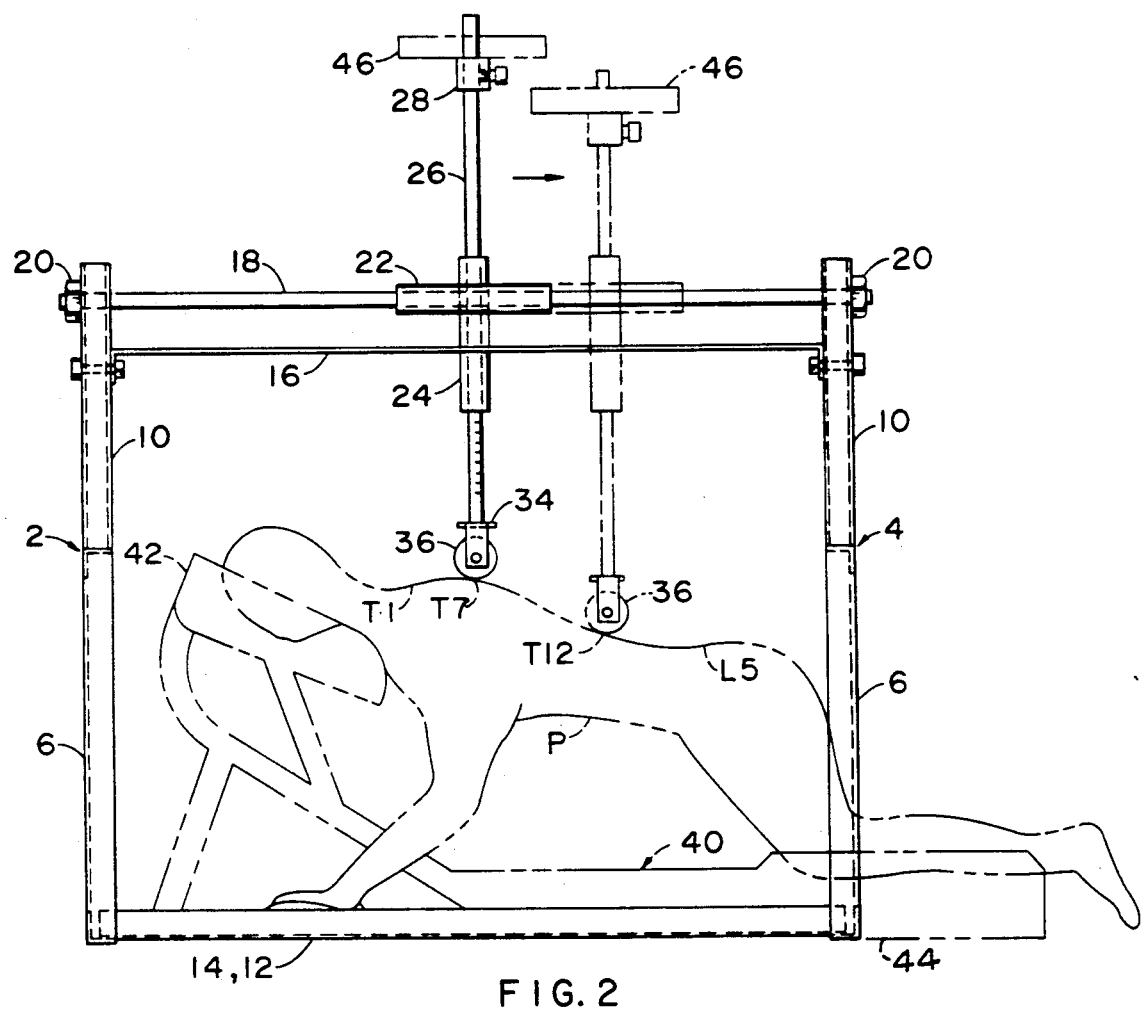
FIG. 2 is an elevation of the device of FIG. 1 with a patient positioned for testing.
Figure 3:
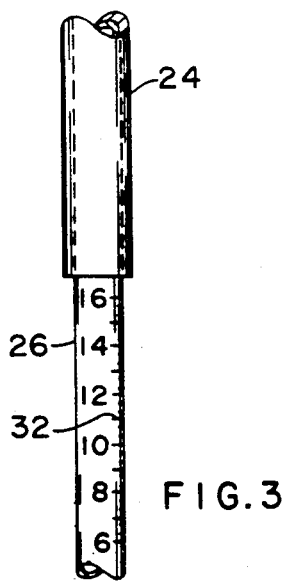
FIG. 3 is an enlarged view of the measuring means of FIG. 1.

Referring more particularly to FIGS. 1 to 3 of the drawings, reference numerals 2 and 4 indicate spaced apart vertical frame supports. Each support includes a lower rectangular portion 6 having an opening 8 therethrough and a vertical leg 10 extending upwardly therefrom. The frame supports 2 and 4 are connected at their bottom by angles 12 and 14, and at their tops by stabilizer 16 and a rod or pipe 18. The frames 2 and 4 may be made from any suitable material such as steel angles for the rectangular portion and a steel rectangular tube for the leg 10 all welded together. The stabilizer 16 may be a steel flat with bent ends bolted to legs 10, Rod 18 has threaded ends extending through legs 10 with nuts 20 threaded thereon. The rod 18 has a sleeve 22 thereon with a close fit and is slidable thereon. A vertical sleeve 24 is welded to sleeve 22 and a rod 26 slidably mounted therein. Downward movement of rod 26 is limited by a weight holder 28 secured thereon by means of a screw 30 adjacent the top thereof. The rod has calibrations 32 thereon preferably in the metric system. An inverted U-shaped member 34 secured to the bottom of rod 26 rotatably supports a rubber wheel 36 on axle 38. The wheel 36 is preferably 3 inches wide and 2½ inches in diameter.

The thoracic vertebrae from top to bottom may be referred to as T1 to T12 and L1 to L5 as the lumbar vertebrae and spinal scans may start the cervical vertebrae and run the entire course of the spine to L5. The midback extends from T7 to L1 and such a scan will be described although it will be understood that all discs may be tested in this manner to measure the anterior to posterior motion of the spinal discs and motor units.

Figure 4:
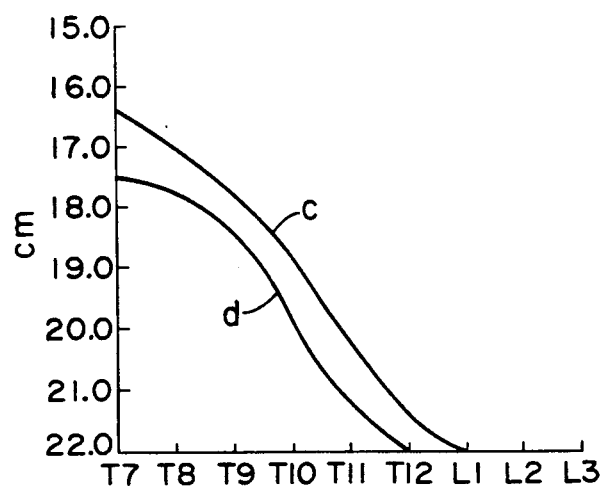
FIG. 4 is a chart of a finished scan.

In carrying out my invention, a standard chiropractic knee-chest table 40 having a headpiece 42 and a kneepiece 44 is positioned as shown in FIG. 2 and the patient P positioned thereon. A standard flat massage table may be used instead with the patient on a flat position, but this provides less accurate results. The wheel 36 is then positioned over the patient's T7 vertebra without the weight 46 in place and the doctor takes a reading on rod 26 at the bottom of the sleeve 24 which is recorded on the chart of FIG. 4. The wheel is then moved successively to each of the vertebra to L1 with each reading recorded on the chart of FIG. 4 and the readings plotted to obtain the curve C. This shows the normal spinal contours because the weight applied is too little to change the contour. This is why the rod 26 is tubular and may also be made of a light weight material.

A weight is then placed on holder 28. This weight is selected by the doctor depending upon the size of the patient. The procedure is then repeated to obtain curve D of FIG. 4 which shows the contour when subjected to a standard force. Thus it can be determined how far the weight caused each vertebra to move so that the doctor can determine the condition of each vertebral disc. For example, he can see that vertebral disc T9 did not move very much so that it is fixated or stuck.

While it is much more expedient to take the readings as set forth it will be apparent that each vertebra could be tested with and without the weight before moving to the next one.

Figure 5:
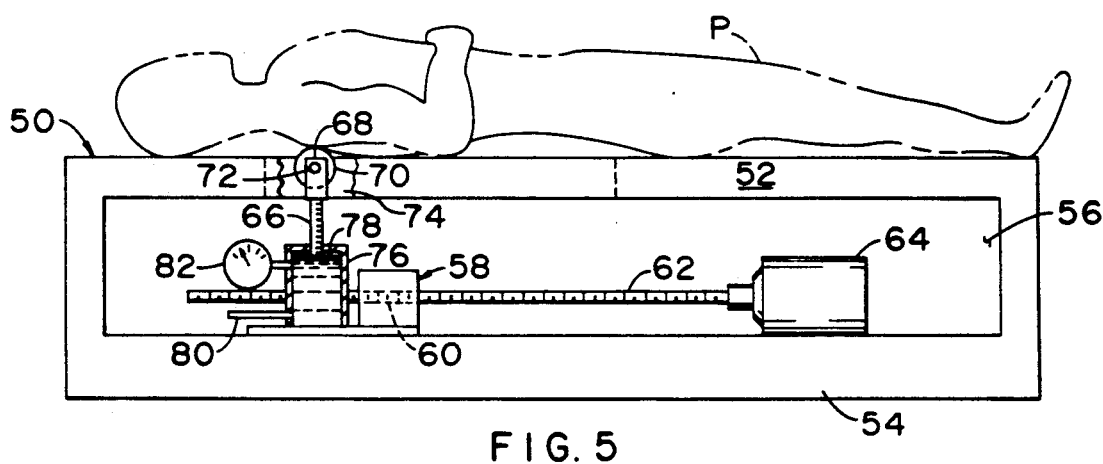
FIG. 5 is an elevation of a second embodiment of my invention.

FIG. 5 shows a second embodiment of my invention in which reference numeral 50 indicates a frame for supporting a patient P upon his back. The frame 50 is box-like, having a top 52 and bottom 54 separated by open space 56 containing the equipment of my invention. This includes a slide 58 mounted for longitudinal movement on the top of bottom 54. The slide 58 has a horizontal longitudinal female threaded section 60 for receiving a longitudinal screw 62 rotatable by a motor 64. A calibrated rod 66, similar to rod 26, is mounted on slide 58 for vertical movement and has a U-shaped member 68 on its upper end for supporting a rubber wheel 70 on transverse axle 72. The rod 66 is kept from turning in any suitable manner such as by making it non-circular in cross section. A longitudinal slot 74 is provided in top 52 to permit roll 70 to contact the patient's back and move along the length thereof. The bottom of rod 66 extends into a fluid cylinder 76 and has a piston 78 mounted thereon. Fluid is supplied to cylinder 76 through pipe 80 and its pressure may be varied in any suitable manner and measured by means of a gage 82.

The operation of this embodiment is substantially the same as that of the first embodiment. With the patient lying as shown, pressure is applied to cylinder 76 just sufficient to hold the roller 70 in firm contact with the spine and a reading taken on rod 66 at the top of cylinder 76. The motor 64 is actuated to move the slide 58 from vertebra to vertebra with a reading being taken at each vertebra and recorded as in the first embodiment. A standard elevated pressure is then applied to cylinder 76 and readings taken and recorded for each vertebra to obtain curves as in FIG. 4. The standard elevated pressure can be varied depending on the patient's size.

It will be understood that the pressure may be applied in other ways to obtain the normal position of a contact member on a disc and its position on the same disc at an elevated pressure. For example, a pulsating or vibrating member may be placed on a disc and the feedback read to determine the variation of the spine position from the low to high portion of the vibrations. It will be understood that the control member does not directly contact the disc but the skin above the disc.

Rotational intervertebral joint dysfunction can be determined using the same apparatus but using a narrower roller.

One approximately ¼ inch wide is suitable. This roller is run down the spine in the same manner as before, but with the roller no closer than ½ inch from the spinous processes, first to the left and then to the right of the spinous processes. As before the first scan on each side would be a tracing with minimal pressure and the second tracing with the higher pressure. The difference on each side would indicate areas of hyper or hypo-mobility in a plane perpendicular to the longitudinal axis of the spine. Left to right comparisons at each level are readily obtained.

While several embodiments of my invention have been shown and described, it will be apparent that other adaptations and modifications be made without departing from the scope of the following claims.

I claim:

1. A method of testing a human spine for mobility, which method comprises steps of contacting a disc of said spine with a spinal contact member under a low enough force to obtain a first position of said contact member while the disc is in its normal position, contacting said disc with said spinal contact member under a steady increased standard force to obtain a second position of said contact member, performing the foregoing steps on a plurality of discs along the spine, determining the distance between the first and second positions of said contact member for each of said discs to determine the mobility of each disc, and recording the first and second positions.

2. The method according to claim 1 in which the recording includes plotting a first curve of said first positions to indicate a tracing of the patient's spine, and plotting a second curve of said second positions adjacent said first curve.

3. A method according to claim 2 in which said contact member is a rotatable roller which rolls along said spine from disc to disc.

4. A method according to claim 3 in which said contact member is a rotatable roller which rolls along said spine from disc to disc.

5. A method according to claim 4 in which said patient rests on his back with an opening below his spine, and said standard force is provided from below.

6. A method according to claim 1 in which said steps are performed on each side of the spinous processes of each of said discs and at least ½ inch therefrom.

7. The method of testing a human spine for mobility, which method comprises contacting a disc of said spine with a spinal contact member under a low enough force to obtain a first position of said contact member while the disc is in its normal position, contacting said disc with said spinal contact member under an increased standard force to obtain a second position of said contact member, comparing the first and second positions of said contact member to determine the mobility of said disc, performing the foregoing steps on a plurality of discs along the spine, plotting a first curve of said first position to indicate a tracing of the patient's spine, and plotting a second curve of said second positions adjacent said first curve.

8. A method according to claim 7 in which said contact member is a rotatable roller which rolls along said spine from disc to disc.

9. A method according to claim 8 in which said patient rests in a position with his face downward, and said standard force is provided by a weight.

10. Apparatus for testing spinal discal motion and resilience comprising a discal spinal contact member, means for holding said contact member against a disc under a minimal pressure, means for increasing the pressure of said contact member against said disc a standard amount, means for supporting a human body with the spine in a generally horizontal position, said contact member being movable along said spine to enable a plurality of discs to be tested, and mans for indicating the position of said contact member under said minimal and increased pressures.

11. Apparatus according to claim 10 in which said contact member is a rotatable roller.

12. Apparatus according to claim 11 including means for moving said roller along the spine.

13. Apparatus according to claim 12 in which said means for holding said contact member against a disc includes a rod extending upwardly from and supporting said roller, a vertical sleeve attached to said means for moving said roller along the spine and through which said rod passes, means attached to said rod above said sleeve to limit its downward movement, and a standard weight detachably secured to said rod above said sleeve.

14. Apparatus according to claim 13 in which said means for indicating the position of said roller includes calibrations on said rod where it enters the lower end of said sleeve.

15. Apparatus according to claim 10 in which said human body rests on its back with no support directly under its spine and in which said means for holding said contact member against a disc includes a rod for extending downwardly from said disc and for supporting said contact member, said rod having a lower end, means for applying upward pressure to the lower end of said rod, and means for moving said rod longitudinally of said spine.

* * * * *